United States Patent
Pedrini et al.

(10) Patent No.: US 6,821,441 B2
(45) Date of Patent: Nov. 23, 2004

(54) METHOD FOR THE PURIFICATION OF BLOOD BY MEANS OF HEMODIALYSIS AND/OR HEMOFILTRATION AND APPARATUS FOR PERFORMING SAID METHOD

(75) Inventors: Luciano Pedrini, Sondrio (IT); Gerhard Wiesen, Eppstein (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 09/900,450

(22) Filed: Jul. 9, 2001

(65) Prior Publication Data
US 2002/0023880 A1 Feb. 28, 2002

(30) Foreign Application Priority Data
Jul. 7, 2000 (EP) .............................................. 00114654

(51) Int. Cl.[7] .......................... B01D 61/32; B01D 61/28
(52) U.S. Cl. .......................... 210/739; 210/85; 210/87; 210/90; 210/97; 210/102; 210/103; 210/134; 210/143; 210/321.65; 210/645; 210/646; 210/650; 210/740; 210/741; 210/746
(58) Field of Search ............................. 210/85, 87, 90, 210/97, 102, 103, 134, 321.65, 645, 646, 650, 739, 740, 741, 143, 746

(56) References Cited
U.S. PATENT DOCUMENTS
5,578,223 A   11/1996   Bene et al. ................... 210/85

FOREIGN PATENT DOCUMENTS

| DE | 42 40 681 | 6/1994 |
|---|---|---|
| EP | 0 358 873 | 3/1990 |
| WO | 98/50091 | 11/1998 |
| WO | 00/09182 | 2/2000 |

OTHER PUBLICATIONS

Pedrini et al.; Abstract at the EDTA/ERA Congress in Madrid; 1999.

Drukker et al.; Replacement of Renal Function by Dialysis; 4th edition, 1996, "Hemodialysis Machines and Monitors", Polaschegg et al.

Primary Examiner—John Kim
(74) Attorney, Agent, or Firm—Jacobson Holman PLLC

(57) ABSTRACT

The present invention refers to a method for blood purification by means of hemodialysis and/or hemofiltration, wherein to the blood in the extra-corporeal circuit of the hemodialysis and/or hemofiltration device a substitution solution is added upstream as well as downstream of the hemodialyser and/or hemofilter. A purification effect remaining constant with a high purification performance is achieved in that one or several of the operational and/or blood parameters are controlled and that the control is carried out using at least one of the infusion rates of the substitution solutions supplied upstream or downstream of the hemodialyser and/or hemofilter. The present invention also refers to a hemodialysis and/or hemofiltration apparatus for the performance of the inventive method.

13 Claims, 2 Drawing Sheets

METHOD FOR THE PURIFICATION OF BLOOD BY MEANS OF HEMODIALYSIS AND/OR HEMOFILTRATION AND APPARATUS FOR PERFORMING SAID METHOD

BACKGROUND OF THE INVENTION

1. Field of the Invention

The present invention refers to a method for blood purification by means of hemodialysis and/or hemofiltration, wherein to the blood in the extra-corporeal circuit of the hemodialysis and/or hemofiltration device a substitution solution is added upstream as well as downstream of the hemodialyser and/or hemofilter.

2. Description of the Related Art

In "Replacement of Renal Function by Dialysis" (Drukker, Parsons and Maher; Kluwer Academic Publishers, $4^{th}$ edition 1996; "Hemodialysis Machines and Monitors" by H.-D. Polaschegg and N. W. Levin)—to the disclosure of which is explicitly referred hereby—a summary of most important hemodialysis procedures and machines is given:

In hemodialysis the blood of a patient is fed through an arterial blood line into the blood chamber of a dialyser. The blood is usually transported by means of a rotary peristalic pump arranged in the arterial blood line. After passing the pump blood is fed through the blood chamber of the dialyser and finally through a venous drip chamber and a venous blood line connected thereto back to the patient. A venous pressure monitor is connected to the venous drip chamber as a protective system for immediate detection of blood loss to the environment. If necessary two needles required for the arterial and venous cannula may be replaced by a single needle in the so-called single-needle-dialysis. In this mode of dialysis, the extra-corporal circuit consists of a single needle cannula with connected Y-piece. From the dialyser the venous line leads back to the Y-piece. The arterial and venous line are occluded alternately by clamps. One or more blood pumps run to manage the alternate flow to and from the Y-piece.

In hemodialysis the solute removal from the blood is driven by diffusion through the dialyser membrane. Though in addition a small transmembrane pressure is applied in order to ultrafiltrate excessive water of a patient, this filtration hardly plays a role for the purification of the blood from specific substances.

Solute removal in hemofiltration is driven by convection rather than by diffusion. At the same time ultrafiltrate is almost entirely replaced by a substitution fluid of a composition similar to dialysate in dialysis. This method emphasizes the similarity to the natural kidney and the more effective removal of larger molecules. On the other hand removal of low molecular substances is reduced as compared to hemodialysis because at best 45% of blood can be ultrafiltrated in the so-called post-dilution hemofiltration. Today, hemofiltration is only used in a small number of patients because of the high cost of commercial replacement fluid and the high blood flow required to perform the treatment in a reasonable time.

Hemofiltration machines for chronic treatment comprise the same extracorporeal pumping and monitoring systems as hemodialysis machines. The dialysate circuit is replaced by a fluid balancing and warming system. In the so-called pre-dilution mode substitution fluid is added to blood upstream of the dialyser and the filtrate is produced by the corresponding transmembrane pressure. To be clinically effective a very large amount of substitution fluid is required. Because of the high cost of commercial substitution fluid this method never became widely accepted. More common is the post-dilution mode because less substitution fluid is required. In this mode the substitution fluid is added to the blood downstream of a dialyser. In the post-dilution mode good purification coefficients are obtained. During a 4 hour treatment normally approximately 20 to 24 liters of substitution fluid are added. The efficiency of the method is, however, limited by a critical transmembrane pressure above which blood damage will occur.

Various systems have been proposed for fluid balancing. In the gravimetric balancing method ultrafiltrate may be withdrawn by the ultrafiltrate pump into a bag or container hanging or standing on a balancing platform. Substitution fluid from a bag or container on the same platform is pumped by another pump to the venous drip chamber. Net fluid removal is achieved either by an additional ultrafiltration pump or by a programming unit that controls the substitution pump to deliver less fluid than removed by the filtration pump.

Hemodiafiltration, a combination of hemodialysis and hemofiltration, can be performed by combining the extracorporal circuits of a hemofiltration and a hemodialysis machine. Hemodialysis machines with volumetrically controlled ultrafiltration can be adapted easily for hemodiafiltration which is more cost-effective. This is particularly cost-effective if the substitution fluid is prepared online from the dialysis fluid.

Treatment parameters such as dialysate contents (sodium concentration), ultrafiltration rate, blood and dialysate flow are varied intradialytically in an attempt to increase or maintain efficacy and/or reduce intradialytic symtoms. The variation either follows a kinetic model or, more often, "clinical judgement". Intradialytic symptoms, especially hypotension, are closely related to ultrafiltration. In dialysis machines having ultrafiltration pumps independent of dialysate pumps, profiling is performed by variation of the ultrafiltration speed.

To summarize in hemodialysis the blood of the patient is purified in that the substances of the blood which have to be removed diffuse through the membrane due to a concentration gradient across the membrane of the dialyser and thereby reach the dialysis fluid. The driving force in hemofiltration is substantially a pressure difference across the membrane which effects a convective transport of substances through the membrane and in doing so cleans the blood above all also from higher-molecular substances. In hemofiltration as well as in the combined method of hemodiafiltration, fluid is removed from the patient blood which has to be substituted except a small difference amount for the control of the fluid balance.

The relatively low efficiency of the pre-dilution mode, especially for low-molecular substances, results from the low concentration gradient across the membrane caused by the dilution and the fact that a purification of the blood as well as of the added substitution liquid is carried out. For the pre-dilution mode, the amounts of substitution fluid added during a 4 hour treatment lie in a range between 40 to 50 liters.

Pre-dilution is used preferably for patients who have a higher risk of coagulation or clotting of the blood. Said risk is reduced by the dilution of the blood prior to blood treatment wherein the cited disadvantages are accepted.

As mentioned above disadvantages occur in post-dilution as it has to be worked with high hemoconcentrations. With respect thereto the hemoconcentrations in predilution are low at least in the entrance section of the hemodialyser and/or hemofilter. Low hematocrit concentrations result in correspondingly large amounts of free water, i.e. unbound water, which renders possible a distinct convective substance transport through the membrane. Correspondingly, the purification effect for middle- and high-molecular substances may be higher in the pre-dilution mode than in the post-dilution mode.

To couple the advantages of the pre- and post-dilution mode it has also been proposed to apply both modes simultaneously with a fixed ratio of pre- and post-dilution substitution fluid flow (L. Pedrini and V. De Cristofaro, Abstract at the EDTA/ERA Congress in Madrid, 1999).

A further disadvantage of the post-dilution mode is that during the blood purification a limiting membrane is built up at the membrane of the hemodialyser and/or hemofilter. The thickness of this membrane increases with increasing duration of treatment, which reduces the permeability of the membrane. Thereby—if the transmembrane pressure remains constant—the purification effect is deteriorated. If a constant purification effect was to be achieved, an increasing trans-membrane pressure would be required which can lead to a damaging of the membrane.

U.S. Pat. No. 5,578,223 discloses an artificial kidney working in the post-dilution mode and being adaptable for use in hemofiltration, hemodialysis and hemodiafiltration treatment. For maintaining a desired concentration of bicarbonate in the blood of a patient the apparatus comprises means for perfusing a liquid containing bicarbonate into the extracorporal blood circuit after passing the exchanger and dosage means for adjusting the bicarbonate concentration in the blood of a patient to a desired level. An extraction pump which is connected to the outlet of the exchanger is controlled by a control unit to obtain a desired level of weight loss during the treatment session. The flow rate of bicarbonate solution is controlled by the control unit as a function of the flow rate of the extraction pump, the desired bicarbonate concentration in the blood of a patient and of the concentration of the bicarbonate solution before perfusion into the extracorporal circuit.

SUMMARY OF THE INVENTION

It is the object of the present invention to provide a method for the blood purification by means of hemodialysis and/or hemofiltration by means of which the advantages of the post-dilution mode and pre-dilution mode can be combined and at the same time the purification effect of the hemodialyser and/or hemofilter remains constant.

Proceeding from a method of the generic type, said object is solved in that one or several of the operational and/or blood parameters are controlled and that the control is carried out using at least one of the infusion rates of the substitution solutions supplied upstream or downstream of the hemodialyser and/or hemofilter.

By adding substitution solutions to the extra-corporeal circuit upstream and downstream of the hemodialyser and/or hemofilter, on the one hand the advantages of the post-dilution and pre-dilution can be combined, i.e. satisfying purification results are obtained for low-molecular substances as well as for middle- and high-molecular substances. On the other hand, according to the invention the infusion rates of one or both of the substitution fluids supplied upstream and downstream are used for the control of operational and/or blood parameters.

Thus, for instance in case of a high trans-membrane pressure or a high hematocrit value of the blood, the infusion rate of the substitution solution added upstream of the dialyser can be increased until the desired values for the values to be controlled are achieved or the values fall below given limiting values. Correspondingly, in case of a low trans-membrane pressure or a low hematocrit value, the infusion rate of the substitution fluid supplied downstream of the dialyser can be increased which, due to the then resulting larger concentration gradient across the membrane leads to an improvement of the diffusive substance transport, i.e. to an improved purification effect for low-molecular substances.

According to a preferred embodiment of the present invention the operational and/or blood parameters are the trans-membrane pressure and/or the blood density and/or the hematocrit value of the blood.

The infusion rate of the substitution solutions supplied upstream of the hemodialyser and/or the hemofilter is preferably increased relative to the infusion rate supplied downstream of the hemodialyser and/or the hemofilter with increasing trans-membrane pressure and/or increasing blood density and/or increasing hematocrit value of the blood.

According to a preferred embodiment of the present invention the operational and/or blood parameters are detected continuously.

It is particularly advantageous when the infusion rates of the substitution solutions are chosen such that a substantially stationary limiting membrane is formed on the side of the membrane of the hemodialyser and/or hemofilter facing the chamber through which the blood flows. Therefrom results the advantage that the efficiency and the sieving-coefficient spectrum of the hemodialyser and/or hemofilter remain constant during the time of treatment.

In a further embodiment of the present invention the relation of the infusion rates of the substitution solutions in the blood stream is changed after termination of the treatment in order to dissolve the limiting membrane. Thereby a major part of the proteins forming the limiting membrane can be supplied back to the patient after finishing the blood treatment.

The present invention also refers to a hemodialysis and/or hemofiltration apparatus with an extra-corporeal circuit for receiving the blood to be purified as well as with a hemodialyser and/or hemofilter communicating with the blood circuit, wherein, upstream and downstream of the hemodialyser and/or hemofilter, the blood circuit has at least one supply line, respectively, for supplying substitution fluid. According to the invention, a control unit for controlling one or several operational and/or blood parameters is provided, wherein the control unit is designed such that the control is carried out by means of at least one of the infusion rates of the substitution solution.

In a preferred embodiment of the present invention measuring devices connected to the control unit are provided for recording the operational and/or blood parameters. Therein said measuring devices can comprise pressure sensors arranged in the extra-corporeal circuit and/or in the dialysis-fluid circuit upstream and/or downstream of the hemodialyser and/or hemofilter, respectively.

In a further embodiment of the present invention the measuring devices comprise sensors in the extra-corporeal circuit upstream and/or downstream of the hemodialyser and/or hemofilter for the detection of the hematocrit value.

In accordance to a further embodiment of the present invention the measuring devices comprise sensors in the extra-corporeal circuit upstream and/or downstream of the hemodialyser and/or hemofilter for the detection of the blood density. According to these preferred embodiments the operational and/or blood parameters are the transmembran pressure and/or the blood density and/or the hematocrit value of the blood.

According to a preferred embodiment means for controlling the at least one of the infusion rates ($Q_s$pre, $Q_s$post) are pumps in the supply lines.

In a further embodiment means for controlling the at least one of the infusion rates ($Q_s$pre, $Q_s$post) are valves 16, 17 in the supply lines.

BRIEF DESCRIPTION OF THE DRAWINGS

Further details and advantages of the present invention will be explained by means of an embodiment represented in detail in the drawing, wherein.

DETAILED DESCRIPTION OF THE PREFERRED EMBODIMENTS

Figure 1:
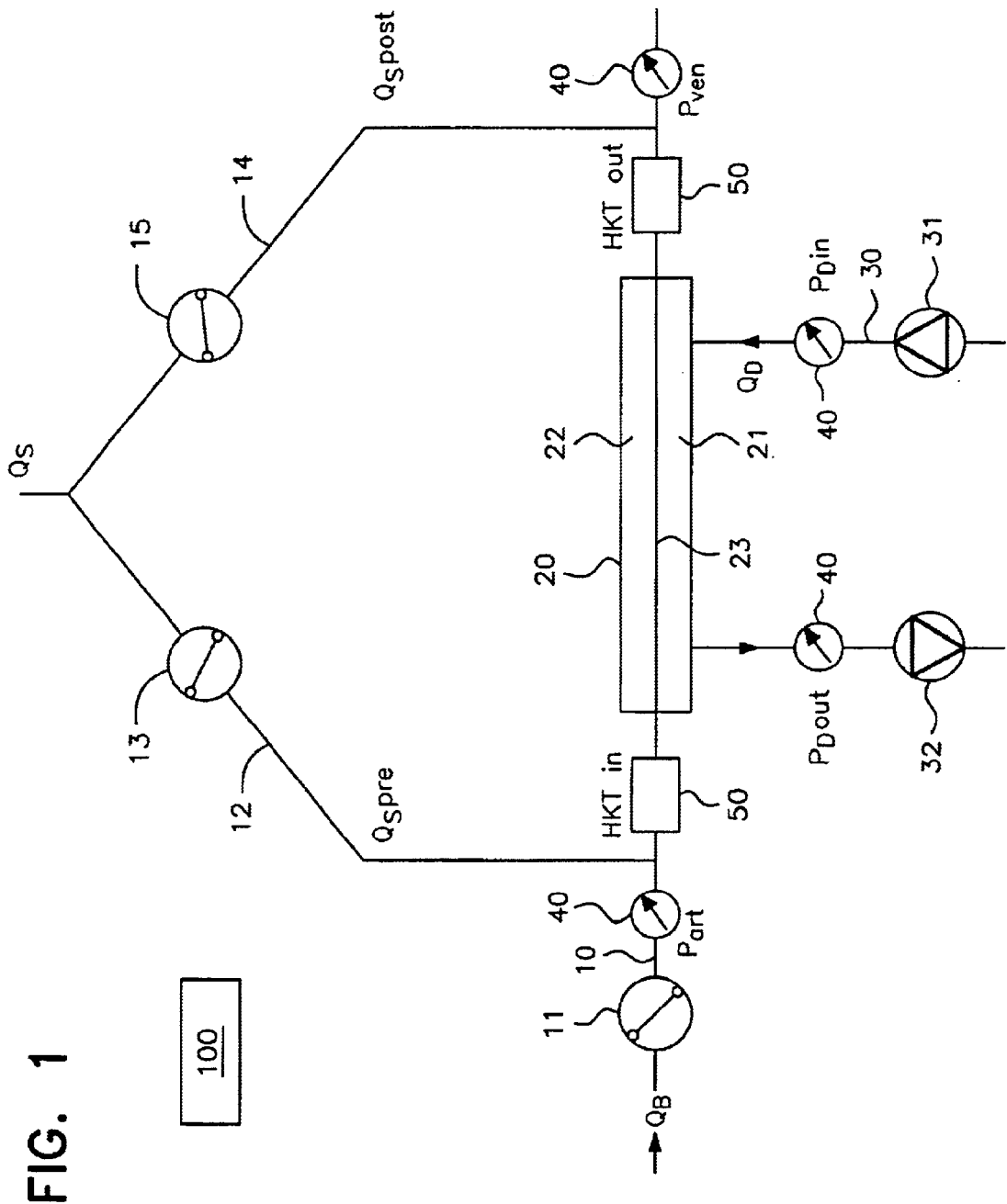
FIG. 1 is a schematic representation of a part of the extra-corporeal circuit as well as of the dialysis fluid circuit with hemodialyser and hemofilter as well as supply lines for the substitution fluid.
Figure 2:
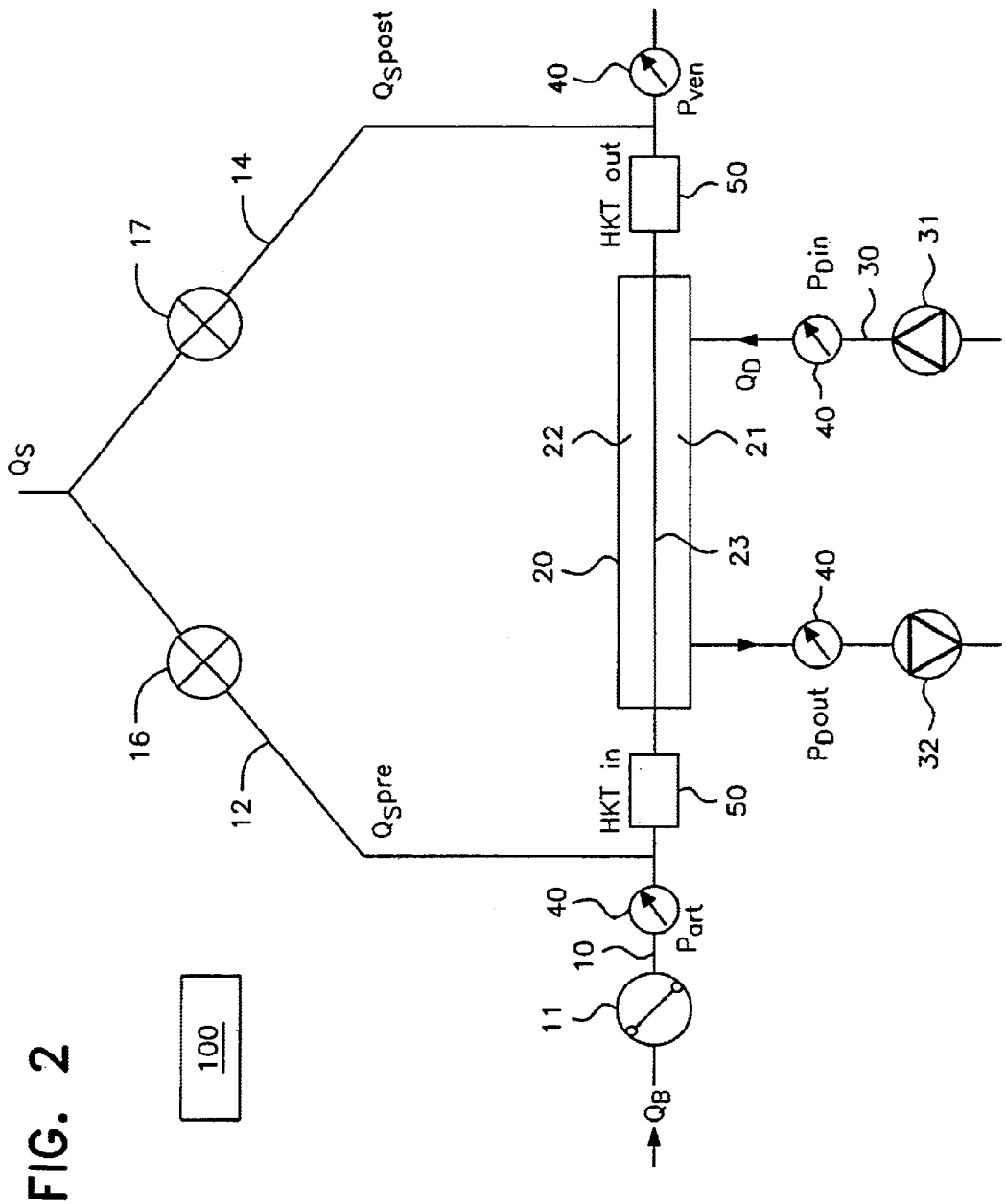
FIG. 2 shows a schematic representative of a part of the extra-corporeal circuit, dialysis fluid circuit with hemodialyser and hemofilter as well as supply lines for the substitution fluid according to an alternative embodiment of the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Downstream of the hemodialyser and/or hemofilter 20 there are arranged corresponding measuring devices 40, 50 for the detection of the corresponding values $p_{ven}$ and $HKT_{out}$ after the blood purification.

In the counterflow to the blood flow, dialysis fluid flows through the hemodialyser or hemofilter 20 with the flow rate $Q_D$ in the direction of the arrow. The dialysis fluid line 30 has pressure sensors 40 upstream as well as downstream of the hemodialyser or hemofilter for the respective pressure $p_D$in and $p_D$out of the dialysis fluid. The circulation of the dialysis fluid is controlled by pump and/or balancing means 31 and 32.

The hemodialyser and/or hemofilter is divided by a semipermeable membrane 21 into a blood chamber 22 and a dialysis fluid chamber 23.

Upstream and downstream of the hemodialyser or hemofilter 20 there are provided supply lines 12, 14, with fluid pumps 13, 15 respectively, by means of which substitution fluid is supplied to the blood flowing in the extra-corporeal circuit 10 during the treatment. The respective flow rates are characterized with $Q_s$pre and $Q_s$post.

Both infusion rates $Q_s$pre and $Q_s$post of the substitution fluid can be varied according to the invention by means of a control unit 100. The control unit 100 is connected to all shown actuators and sensors by not shown connections. The variation of the infusion rates is carried out in accordance with the measuring values of the control values to be controlled. According to the embodiment shown in FIG. 1 the measuring values are the arterial and venous blood pressure $p_{art}$, $p_{ven}$ as well as the pressure of the dialysis fluid $p_D$in and $p_D$out prior to and after passing the hemodialyser and hemofilter 20. The trans-membrane pressure TMP determined therefrom is adjusted according to the invention by a suitable variation of the flow rates $Q_s$pre and $Q_s$post to the desired target value or is maintained at said value. Instead of the trans-membrane pressure TMP the hematocrit values $HKT_{in}$, $HKT_{out}$ may be used as control values. The TMP may also be approximated by less than the shown four pressure sensors. In current dialysis machines it is common to use pressure sensors only for $p_{ven}$ and $p_D$out.

By using the claimed method or the claimed apparatus it is achieved that the limiting membrane building up on the side of the membrane of the hemodialyser or hemofilter facing the chamber in which the blood is present can be kept in a stationary state which results in a constant purification spectrum as well as a constant degree of purification during the treatment. At the same time the transmembrane pressure can be kept constant during the treatment, as the pressure loss caused by the membrane and the limiting membrane also remains constant.

By the limitation of the trans-membrane pressure to a predeterminable value the danger of an extensive loss of albumin through the membrane caused by large convective forces can be prevented. If high-flux membranes are used the limitation of the trans-membrane pressure is particularly important.

Especially for patients with strong coagulation problems the combination of pre- and post-dilution also helps to reduce the heparin consumption which is usually infused into the blood to avoid blood coagulation in the extra-corporal circuit. If the blood is diluted upstream the hemodialyser and/or hemofilter, less anti-coagulating fluid is required to reduce the danger of blood coagulation in the hemodialyser and/or hemofilter as the latter represents the most significant potential for blood coagulation in the extra-corporal blood circuit.

Apart from the above mentioned advantages of a constant operational behavior, by the combination of pre-dilution and post-dilution good purification performances for low-molecular as well as middle- and high-molecular substances can be obtained.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A method for blood purification by means of hemodialysis and/or hemofiltration using a hemodialysis and/or hemofiltration device having an extra-corporeal blood circuit in communication with a hemodialyser and/or hemofilter that is divided by a membrane, said blood circuit having an upstream supply line and a downstream supply line upstream and downstream, respectively, of said hemodialyser and/or hemofilter for supplying a substitution fluid, said hemodialysis and/or hemofiltration device further including a control unit connected to a measurement device, the method comprising the steps of:

receiving in said extra-corporeal blood circuit blood to be purified;

measuring by said measurement device at least one operational and/or blood parameter within the received blood, said operational and/or blood parameter being selected from the group consisting of trans-membrane pressure, hematocrit value and blood density;

controlling, by said control unit, at least one of an infusion rate ($Q_s$pre) of said upstream supply line and an infusion rate ($Q_s$post) of said downstream supply line, in response to said step of measuring in order to control said at least one operational and/or blood parameter.

2. The method according to claim 1, wherein said step of controlling includes increasing the infusion rate ($Q_s$pre) of said substitution fluid through said upstream supply line relative to the infusion rate ($Q_s$post) through said downstream supply line when, in response to said step of measuring, it is determined that at least one of said transmembrane pressure, said hematocrit value and said blood density is increasing.

3. The method according to claim 1, wherein said steps of measuring and controlling are performed continuously during said blood purification.

4. The method according to claim 1, further comprising the step of selecting said infusion rates ($Q_s$pre, $Q_s$post) such that a substantially stationary limiting membrane is formed on a side of the membrane of the hemodialyser and/or hemofilter facing a chamber through which the blood flows.

5. The method according to claim 4, wherein upon termination of said blood purification, the limiting membrane is dissolved by changing a relation of said infusion rates ($Q_s$pre, $Q_s$post) of said substitution fluid in the blood.

6. A hemodialysis and/or hemofiltration apparatus comprising:
- an extra-corporeal blood circuit for receiving blood to be purified;
- a hemodialyser and/or hemofilter communicating with said blood circuit;
- said blood circuit having an upstream supply line and a downstream supply line upstream and downstream, respectively, of said hemodialyser and/or hemofilter for supplying a substitution fluid, said upstream supply line having an upstream infusion rate ($Q_s$pre) and said downstream supply line having a downstream infusion rate ($Q_s$post);
- a measuring device including at least one sensor for recording at least one operational and/or blood parameter selected from the group consisting of transmembrane pressure, hematocrit value and blood density; and
- a control unit connected to said measuring device for controlling said at least one operational and/or blood parameter by controlling at least one of said upstream and downstream infusion rates in response to data received from said measuring device.

7. The apparatus according to claim 6, further comprising a dialysis-fluid circuit in communication with said hemodialyser and/or hemofilter, wherein said at least one sensor includes pressure sensors arranged in said extra-corporeal blood circuit and the dialysis-fluid circuit, upstream and downstream of said hemodialyser and/or hemofilter, respectively.

8. The apparatus according to claim 6, wherein said at least one sensor includes sensors arranged in said extra-corporeal blood circuit upstream and downstream of said hemodialyser and/or hemofilter for detecting the hematocrit value of the blood.

9. The apparatus according to claim 6, wherein said at least one sensor includes sensors arranged in said extra-corporeal blood circuit upstream and downstream of said hemodialyser and/or hemofilter for detecting blood density.

10. The apparatus according to claim 6, further comprising pumps in said upstream and downstream supply lines, respectively, said pumps controlled by said control unit to control said infusion rate ($Q_s$pre) and said infusion rate ($Q_s$post).

11. The apparatus according to claim 6, further comprising valves in said upstream and downstream supply lines, respectively, said valves controlled by said control unit to control said infusion rate ($Q_s$pre) and said infusion rate ($Q_s$post).

12. A method for blood purification by means of hemodialysis and/or hemofiltration using a hemodialysis and/or hemofiltration device having an extra-corporeal blood circuit in communication with a hemodialyser and/or hemofilter that is divided by a membrane, said blood circuit having an upstream supply line and a downstream supply line upstream and downstream, respectively, of said hemodialyser and/or hemofilter for supplying a substitution fluid, said hemodialysis and/or hemofiltration device further including a control unit connected to a measurement device, the method comprising the steps of:
- receiving in said extra-corporeal blood circuit blood to be purified;
- measuring by said measurement device at least one operational and/or blood parameter of the received blood;
- controlling, by said control unit, at least one of an infusion rate ($Q_s$pre) of said upstream supply line and an infusion rate ($Q_s$post) of said downstream supply line, in response to said step of measuring in order to control said at least one operational and/or blood parameter; and
- selecting said infusion rates ($Q_s$pre, $Q_s$post) such that a substantially stationary limiting membrane is formed on a side of the membrane of the hemodialyser and/or hemofilter facing a chamber through which the blood flows.

13. The method according to claim 12, wherein upon termination of said blood purification, the limiting membrane is dissolved by changing a relation of said infusion rates ($Q_s$pre, $Q_s$post) of said substitution solution in the blood.

* * * * *